United States Patent [19]
Farrell

[11] Patent Number: 5,241,332
[45] Date of Patent: Aug. 31, 1993

[54] TREATMENT MODALITY IN OCCUPATIONAL THERAPY

[76] Inventor: Joyce M. Farrell, 181 Stuyuesant Dr., Selden, N.Y. 11784

[21] Appl. No.: 800,284

[22] Filed: Nov. 29, 1991

[51] Int. Cl.⁵ .............................................. A61B 3/00
[52] U.S. Cl. ...................................... 351/246; 351/203
[58] Field of Search ................................ 351/203, 246

[56] References Cited

U.S. PATENT DOCUMENTS

| | | | |
|---|---|---|---|
| 630,859 | 8/1899 | Carter | 351/203 |
| 2,110,344 | 3/1938 | Taylor et al. | 351/203 |
| 2,451,932 | 10/1948 | Ellis | 351/239 |
| 2,744,441 | 5/1956 | Cox | 351/203 |
| 4,135,502 | 1/1979 | Peck | 351/203 |
| 4,365,873 | 12/1982 | Ginsburg | 351/239 |
| 4,379,699 | 4/1983 | Nelson | 351/239 |
| 4,660,948 | 4/1987 | Retz | 351/203 X |
| 4,979,812 | 12/1990 | Reese | 351/203 X |

*Primary Examiner*—Scott J. Sugarman
*Attorney, Agent, or Firm*—Galgano & Belkin

[57] ABSTRACT

Visual-perceptual, visual-motor, and cognitive training exercises on scanning boards that are large enough to involve visual scanning and tracking sufficient for head turning and full visual field awareness as required for integrating stimuli from the environment. The boards vary in design incorporating perceptual and cognitive subskills which may be modified to all levels of ability. Specifically, the boards are used with clients in occupational therapy who have visual-perceptual, and visual-motor deficits, i.e., due to cerebral vascular accident, head injury, ocular-motor impairments, and other visual deficits, as well as for special education teachers for instruction of students with learning disabilities impaired by perceptual deficits, cerebral palsy, etc. The boards are coated with a non-glare plastic covering and may be drawn on with various colored water-base, odorless, non-toxic pens, as the boards may be wiped clean and ready to be re-used indefinitely.

6 Claims, 2 Drawing Sheets

TREATMENT MODALITY IN OCCUPATIONAL THERAPY

BACKGROUND OF THE INVENTION

This invention relates to the treatment and training of clients who exhibit visual-perceptual and visual-motor deficits following a cerebral vascular accident, head injury, brain tumor, other types of neurological impairments and diseases, opthalmologic injuries, childhood diseases, and learning disability. It may also be used in treatment of apraxia, incorporating tracking motorically as well as visually.

Occupational therapists theorize that for a person to volitionally function in his/her environment he/she must master his/her environment through their relationship with it and its specific components. The task of any goal oriented movement may be done with or without assistance or compensation and may be acquired through the development of a hierarchy of subskills.

Individual occupational therapists who treat such patients try to develop techniques to develop these subskills, but to date no uniform modality has been established which is effective and practical.

A number of United States patents have been issued in the area of eye training.

U.S. Pat. No. 630,859 shows an eye strengthener utilizing a curved member.

U.S. Pat. No. 2,110,344 discloses a device for displaying words.

U.S. Pat. No. 2,451,932 shows an adjustable perimeter target consisting of a curved member with an object that is moved along its surface.

U.S. Pat. No. 2,744,441 illustrates a curved member with means for measuring angles.

U.S. Pat. No. 4,135,502 discloses a device for making stereoscopic patterns.

U.S. Pat. No. 4,365,873 shows a chart for measuring and quantifying visual sensitivity.

U.S. Pat. No. 4,379,699 discloses a method and apparatus for improving the reading efficiency of persons with specific dyslexia, involving in part the highlighting of background.

None of the preceding patents teaches the present invention.

SUMMARY OF THE INVENTION

In this invention a modality of treatment is defined which if followed by trained occupational therapists will train brain injured patients to successfully compensate for losses in certain vision fields and awareness.

In accordance with the principles of this invention, scanning boards are used to provide an array of visual-perceptual, visual-motor, and cognitive activities necessary for information processing of the environment. Positioning of the boards may be altered between being presented on an incline directly in front of the client and being flat on the table top. The boards incorporate training of perceptual skills in the areas of figure-ground, form-constancy, visual-descrimination, design-copy, scanning, position-in-space, spatial-relationship, directionality, and depth and distance perceptual deficits. Cognitive skills incorporated may include problem solving, sequencing, attention to detail and shifting of attention, orientation, organization, following directions, and memory.

Perceptual dysfunction, in combination with cognitive limitations, has a devastating effect on the brain damaged individual from taking advantage of compensatory training, and impaired perception may lead to impaired processing of information from the environment into the cognitive system according to Rosenthal, et al., in "Rehabilitation of the Head injured Adult", 1984, F. A. Davis Company, Pa.).

Visual control, particularly in the stroke client, cannot be overstressed in the treatment of hemiplegia. Frequently there is a visual field (unilateral) neglect associate with hemiplegia (more commonly in the left hemiplegic) in which there is also sensory loss. Dependence on visual scanning, especially when one has a severe sensory loss, is crucial for safety and coordination in motor return of the hemiplegic side. The stroke client will often neglect to see the placement or position of the affected extremity causing danger to himself. The extremity may fall between wheel-chair spokes while propelling the wheelchair, or it may caught between self and furniture or wall when transferring. The client may propel the wheelchair into walls, furnishings, or people on the affected side, or experience danger due to poor balance and judgement.

Poor visual control also hinders coordination activities, integration of body scheme, and attention for symmetrical posturing. Orientation of the affected side is altered because two sides of the body are perceived differently following stroke. Integration in everyday activity, judgement, and equilibrium become drastically reduced and become major treatment issues. The scanning boards encourage voluntary scanning, to either left or right side, incorporating other visual-perceptual tasks necessary for effective and safe functioning.

Visual-motor deficits in head injured persons include diverse impairments such as saccadic eye movements, ocular pursuits, visual scanning, double vision, nystagmus, cortical blindness, homonomous hemianopsia, impairment of global stenosis, diplopia, along with visual-perceptual deficits, which are commonly seen. "The head injured adult may have an unusual variety of visual impairments, involving the retina, optic nerves, or any other portion of the optic radiation, including the visual cortex where the visual signals are interpreted or appreciated", according to Rosenthal et al, supra. The scanning boards are thus able to be utilized in visual training motorically involving eye musculature as well as head turning and compensation strategies in addition to perceptual and cognitive training.

In educating children with special learning needs, symptomatology of visual-perceptual and visual-motor deficits may include letters that collide with each other or no space between words, letters not on line, letters formed in a strange way, mirror writing, inability to color within lines, illegible handwriting, inability to cut, inability to paste, messy papers, and a child holding pencil too tight often breaking pencil or crayon points, according to Harnell in "Complete Learning Disabilities Handbook", 1989, The Center For Applied Research in Education, New York. According to Luftig in "Assessment of Learners With Special Needs", 1989, Allyn and Bacon, Mass., "efficient perceptual abilities functioning is essential to the learner in cognitive, social, and emotional development . . . for some individuals, accurate sensory and perceptual-motor functioning is a problem that can interfere with their ability to learn and interact with the everyday environment in meaningful ways."

One worker in the field has developed a treatment approach that addresses school-related difficulties in a skill-development manner. She advocated analyzing processes involved in task performance and developing underlying subskills in a hierarchial manner that will lead to improved performance. Her holistic, or comprehensive and unified, approach to evaluation and treatment of children with learning disorders involves both the development of underlying sensory and motor organization and the development of foundation abilities more visibly related to academic performance (directionality, sequencing, and problem solving organization, pre-reading skills, fine motor skills for hand writing, and so forth). This is described by Faber in "Neurorehabilitation, A Mulitsensory Approach", 1982, W. B. Saunders Company, Pa.

The relationship between visual-perceptual and visual-motor skills, in conjunction with cognitive skills, and their significance in integration of sensories and their affects on performance in school or otherwise is greatly acknowledged. Eyes should . . . "follow the visual-stimulation in a smooth, fluid, coordinate manner and in coordination with each other. Over shooting or losing the target, difficulty in changing direction, lagging behind, attempting to move the head instead of the eyes, making faces, blinking frequently or squinting, inattentiveness, difficulty in looking away from the visual stimulus or finding it again, inability of the eyes to work together and, especially difficulty crossing midline are each suggestive of less than perfect integration" (Banus, et al. Developmental Therapist, 1979, Slack, N.J.).

The scanning boards used in my invention may be utilized for any population of clients exhibiting visual-perceptual-motor deficits as determined by the occupational therapist or special education teacher. The boards may be used in a variety of fashions and adapted to the particular needs of the individual treatment or educational plan. They are covered with non-glare plastic thus they eliminate visual distractions from light glares. Odorless, non-toxic, water-base multi-colored pens which dry immediately to prevent from smudging during tracking with finger or pointing, which also easily wipes off with dampened cloth are used. A workbook provided may also be written in, and wiped clean. The workbook includes various activities for an array of perceptual and cognitive abilities. The activities may be altered as therapist or teacher sees fit. The boards may be used individually or with a group, and may or many not necessitate one-to-one assistance of a therapist or teacher.

It is therefore a principal object of this invention to provide a treatment modality specific to a certain class of patients requiring the development of compensation for certain consequences of brain injury and related disorders.

Other objects and advantages of this invention will hereinafter become obvious from the following description of preferred embodiments of this invention.

DESCRIPTION OF THE PREFERRED EMBODIMENTS

The scanning boards, to be described below, may conform to any frame of reference by choice of the occupational therapist. Traditionally, visual-perceptual and visual-motor training tasks have been performed on 8.5'×11' paper on table top or incline, as well as block designs, peg designs and computer activities in skill building for transfer of training to functional tasks. Environmental, functional approaches have also been traditional in treatment, utilizing task specific, goal oriented activities, i.e., games, crafts, and ADL specific tasks, whereas both approaches are inherently different in nature. Very little has been done to concretely bridge and blend the two very different approaches of skill building, developmental sequencing and generalization of skills learned with the task oriented, goal specific here-and-now approach of skills learned in everyday tasks. The scanning boards incorporate a gestalt of both functional and theoretical approaches to aid a person with visual-perceptual-motor deficits in acquiring skills effectively while encouraging the individual's interaction with his environment scanning it motorically.

Figure 1:
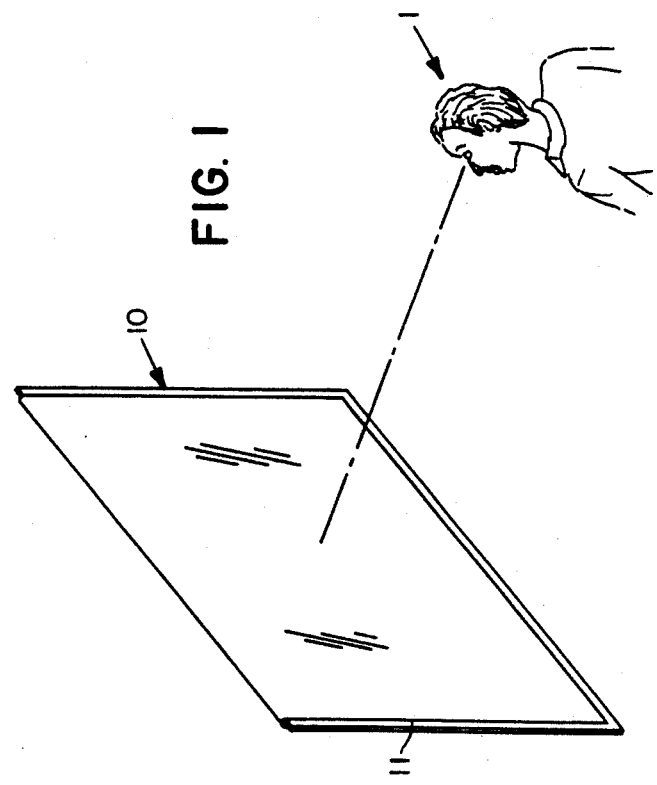
FIG. 1 illustrates schematically a patient facing a scanning board constructed in accordance with the principles of this invention.

Referring to FIG. 1, there is shown a patient 1 placed in a position facing scanning board 10. The size of board 10 in relation to the distance between the eyes of patient 1 is such that patient 1, taking into account his disability, must turn his head side to side in order to read the contents of board 10 fully, from edge to edge. Board 10 would also be supplied with a transparent, plastic overlay 11 on which the therapist or patient can circle information which is on the board underneath. As is understood in the art, the writings on the overlay would be readily removed by a rag or an eraser.

As is understood to therapists who treat such patients, patient 1 is a person who has suffered a stroke or has brain injury as the result of an accident, and among the symptoms the patient evinces is the loss of at least some part of the visual field with poor peripheral vision resulting in a decreased awareness of the surroundings due to the loss of sight.

One of the principal purposes of this invention is to train patient 1 to develop compensation for this disability by having the patient trained to move his head repeatedly from side to side to become aware of his surroundings.

Figure 2:
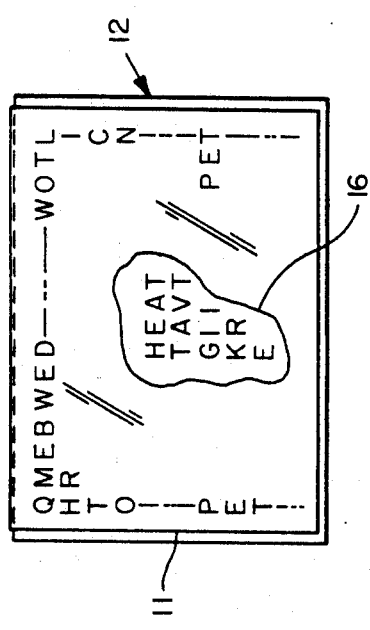
FIG. 2 is a face view of a scanning letter board useful in carrying out the principals of this invention.

For the content of a board to carry out the principles of this invention, reference is made to FIG. 2 wherein is illustrated a letter board 12.

Board 12 is filled with columns and rows of block letters 14 in the manner illustrated. Typically board 12 would be stiff and measure 30 inches wide and 20 inches high, with 13 rows and 24 columns of letters.

As seen in the small inset 16, words would be formed in all directions, for example, "HEAT" in a row, "VAT" in a row but in the opposite direction, "IRE" in a diagonal, and "HAIR" in a column. The therapist would place the patient in a position facing the board and ask the patient to identify on the board the work "PET", for example, and in this case that word appears on opposite ends of the board. Even if the word did not appear on opposite ends of the board, the patient would still have to search the whole board, moving his head side to side in the process. The therapist or patient would circle the letters or words on overlay 18.

Depending on the ability of the patient, longer words or the use of diagonals for the words may be employed.

Figure 3:
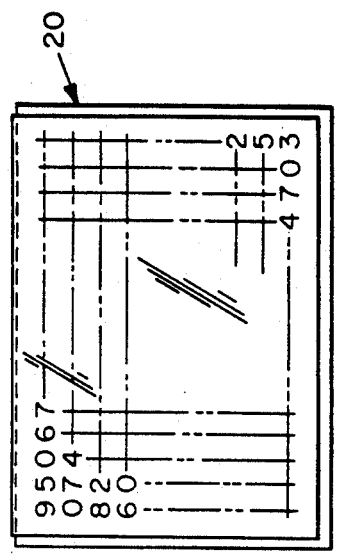
FIG. 3 is a face view of a scanning number board which can be also be employed.

In a similar manner number board 20 shown in FIG. 3 may be employed with numerals 0 to 9 arranged in rows and columns. In the use of this board, the therapist can ask the patient not only to identify numbers, i.e. "506", but also to do simple problems, such as locate pairs of numbers which add up to 16, for example, or even conduct exercises in multiplication or subtraction, helping to stretch the patient's attention span or concentration. Again, as in all the boards being illustrated, the selected items can be circled on the transparent overlay.

Figure 4:
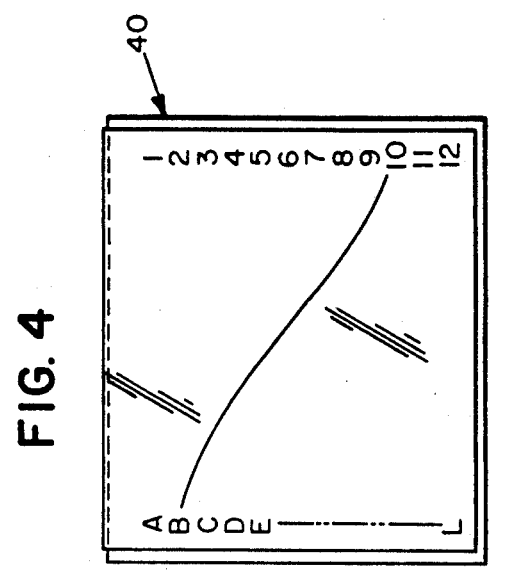
FIG. 4 is a face view of a scanning visual tracking board which also can be employed.

Shown in FIG. 4 is a visual tracking board 40 with columns of numbers and letters on opposite ends of the board. The patient would be asked to draw lines between specific pairs of letters and numbers, as seen drawn between the letter B and numeral 10.

Figure 5:
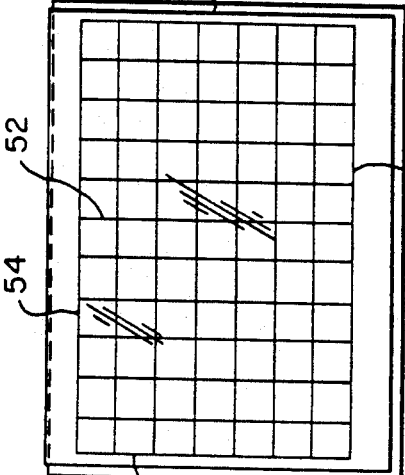
FIG. 5 is a face view of a grid board which can be used.

FIG. 5 illustrates a grid board 50 with vertical and horizontal grid lines 52 and 54 typically spaced apart one inch in both directions, forming squares. On this board, the therapist, or the patient can be requested to form a layout using the grid lines on one part of the board, and the patient can then duplicate the geometric figure elsewhere, possibly enlarged. Also, the patient can be asked to outline on the board the room presently occupied, possibly using different colors for different objects. This is a difficult project for this type of patient because it requires the patient to look around and transfer the images to the board. In addition, a number of games can be played on this board, such as "Battleship", or using different colors to close boxes outlined on the board.

Figure 6:
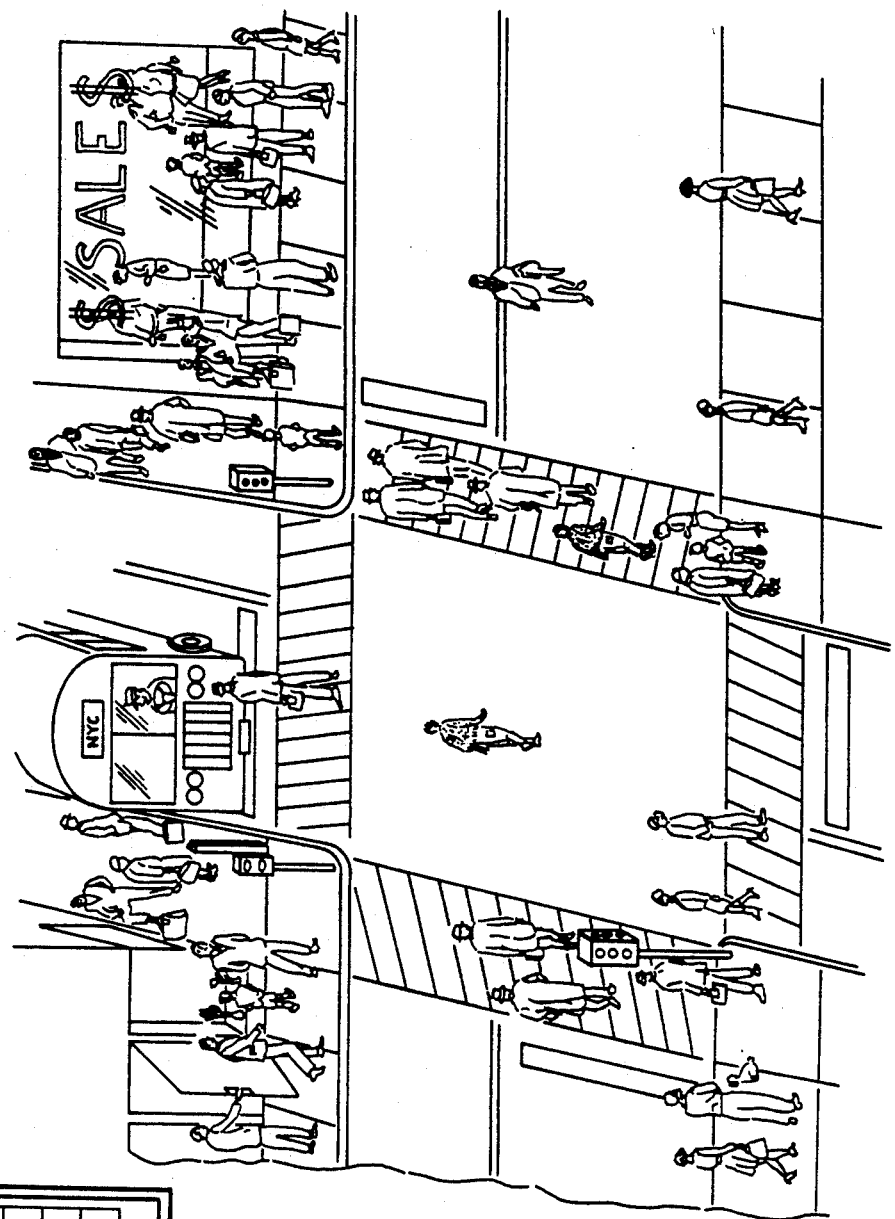
FIG. 6 is a face view of a portion of a city scene board which can be used.

A city board 60 is illustrated in FIG. 6 on which is shown a variety of scenes typically found in the city. The patient could be asked to circle people with hats, women with slacks or coats, and even to narrate what is going on in a particular portion of the board.

It should also be noted that sometimes a blank board can be utilized to make up other challenges that the therapist might develop, using the transparent cover sheet but carrying out the principles of this invention as described above.

The boards should be stiff enough so that no backing is required, and all boards should be provided with the transparent, eraseable cover sheet or overleaf to permit the patient to write on, and yet being able to erase the written material for use with another patient. The boards can be used propped up or lying on the table. In the latter type of use, the patient gazes at the board at an angle thus introducing depth perception into the equation Some patients will find that exercise particularly useful While only certain preferred embodiments of this invention have been described it is understood that many variations are possible without departing from the principles of this invention as defined in the claims which follow.

What is claimed is:

1. A method of conducting therapy for a patient having poor peripheral vision for the purpose of training said patient to move his head repeatedly side to side under normal conditions to improve the patient's awareness of his surroundings comprising the steps of having said patient perform certain exercises consisting of placing in front of said patient a display scanning board which is sufficiently large so that said patient must turn his head repeatedly side to side to be able to see all parts of said board, said board having a transparent plastic overlay for marking with an erasable marker, said board containing bits of information distributed throughout said board, directing said patient to identify specific, similar bits of information located on different parts of said board sufficiently far apart on said board so as to require said patient to move his head side to side to locate said similar bits of information, marking with said marker on said overlay said identified bits of information, and erasing all marks on said overlay to reuse said board with another patient.

2. The method of claim 1 in which said board contains a display of letters in columns and rows, forming words in all directions in rows, columns, and diagonals.

3. The method of claim 1 in which said board contains a display of numerals in columns and rows.

4. The method of claim 1 in which said board contains a display of a column of identifying marks along one edge and a column of identifying marks along the opposite edge, and said patient is instructed to draw a line between identifying marks.

5. The method of claim 1 in which said board contains a grid on which the patient is instructed to copy various geometric figures.

6. The method of claim 1 in which said board displays a scene on which said patient is instructed to circle on said overlay areas of interest as instructed.

* * * * *